United States Patent
Fischer et al.

(10) Patent No.: US 6,183,499 B1
(45) Date of Patent: *Feb. 6, 2001

(54) SURGICAL FILAMENT CONSTRUCTION

(75) Inventors: Jerome A. Fischer, Warren; Howard Scalzo, Kenilworth; Jianguo J. Zhou, Bridgewater, all of NJ (US)

(73) Assignee: Ethicon, Inc., Somerville, NJ (US)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/366,890

(22) Filed: Aug. 4, 1999

Related U.S. Application Data

(60) Provisional application No. 60/099,857, filed on Sep. 11, 1998.

(51) Int. Cl.$^7$ .................................................. A61B 17/04
(52) U.S. Cl. ........................ 606/228; 606/229; 606/230
(58) Field of Search ................................ 606/228, 231

(56) References Cited

U.S. PATENT DOCUMENTS

| | | | |
|---|---|---|---|
| 2,401,291 | * 5/1946 | Smith et al. ........................ | 606/228 |
| 2,735,258 | 2/1956 | Crandall . | |
| 2,824,485 | 2/1958 | Gregory . | |
| 3,791,388 | * 2/1974 | Hunter et al. ........................ | 606/230 |
| 3,982,543 | * 9/1976 | Schmitt et al. ...................... | 606/228 |
| 4,027,676 | 6/1977 | Mattei .................................. | 606/228 |
| 4,043,344 | * 8/1977 | Landi et al. ......................... | 606/228 |
| 4,520,822 | * 6/1985 | Menezes et al. .................... | 606/230 |
| 4,557,264 | * 12/1985 | Hinsch ................................. | 606/229 |
| 4,564,013 | * 1/1986 | Lilenfeld et al. ................... | 606/230 |
| 4,959,069 | * 9/1990 | Brennan et al. ..................... | 606/228 |
| 5,019,093 | * 5/1991 | Kaplan et al. ....................... | 606/228 |
| 5,059,213 | * 10/1991 | Chesterfiled et al. .............. | 606/228 |
| 5,133,739 | * 7/1992 | Bezwada et al. .................... | 606/230 |
| 5,219,659 | * 6/1993 | Weber et al. ........................ | 428/397 |

FOREIGN PATENT DOCUMENTS

WO 86/00020 3/1986 (WO) .

* cited by examiner

Primary Examiner—Gary Jackson

(57) ABSTRACT

We have discovered a surgical filament suitable for use as a suture or ligature that comprises a multifilament core having a plurality of filaments that are oriented having an external surface and internal interstices; and an outer coating that bonded to the external surface of the core but does not penetrate into the internal interstices of the core and a process for making these sutures.

17 Claims, 6 Drawing Sheets

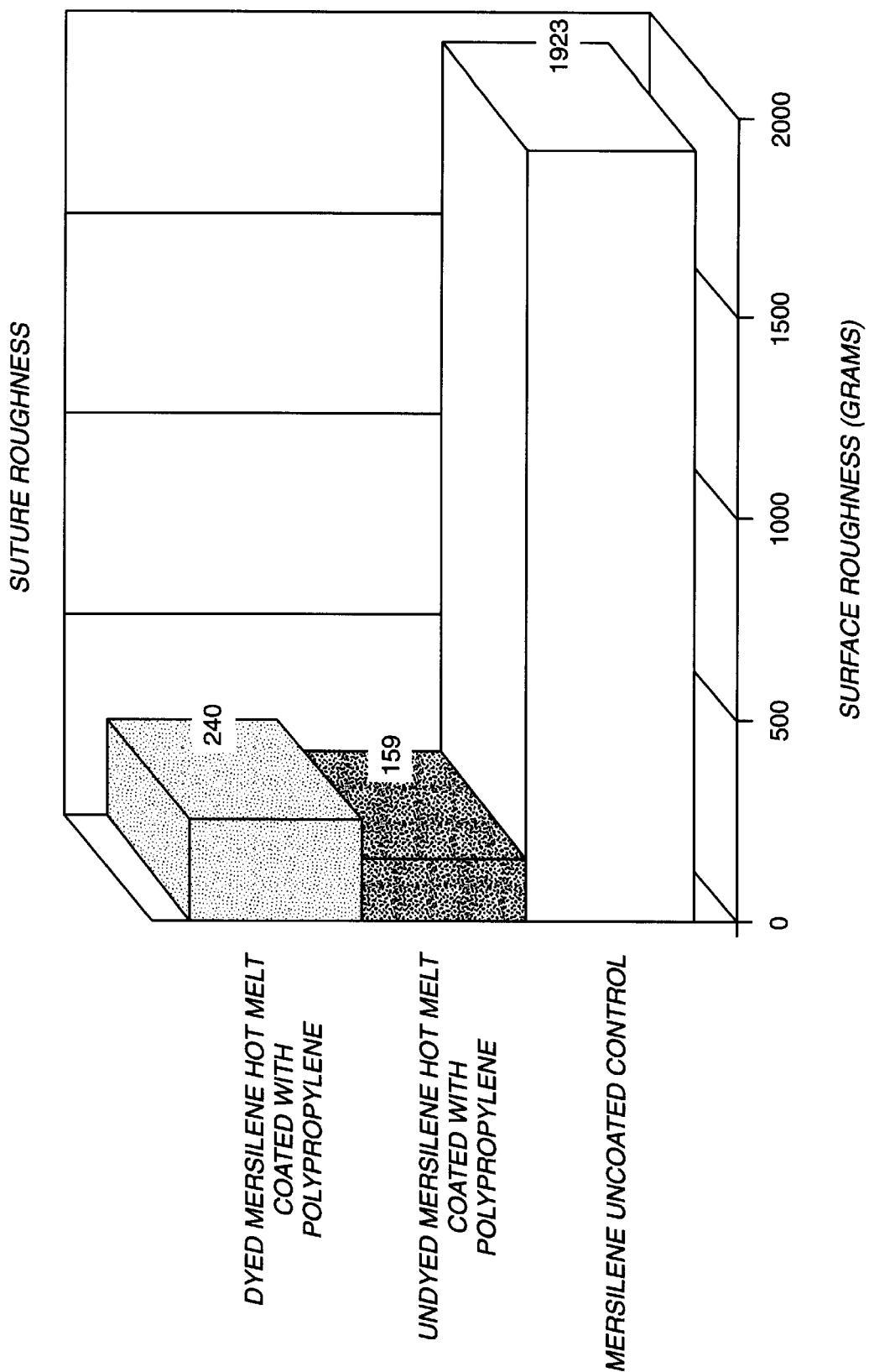

SURGICAL FILAMENT CONSTRUCTION

This Appln claims benefit of provisional appln No. 60/099,857, filed Sep. 11, 1998.

FIELD OF INVENTION

The present invention relates to surgical filaments and more specifically to flexible multifilament sutures with a smooth surface.

BACKGROUND OF THE INVENTION

Multifilament and monofilament sutures are commonly employed in surgical procedures. Multifilament sutures were the first sutures developed from natural fibers such as silk. Multifilament sutures generally have a braided or twisted construction. These constructions provide sutures with significant flexibility and strength. However, multifilament sutures tend to abrade tissue as the sutures are passed through the tissue thereby damaging the tissue. The tissue drag generated by the suture abrasion also requires the surgeon to use more force to overcome the tissue's resistance to the suture. To reduce tissue drag and make it easier for surgeons to tie knots in multifilament sutures, sutures are often solution coated with a lubricious coating. This allows a knot to be tied and slid down easily without the "chatter" normally associated with and uncoated braided suture. Sutures are typically coated by immersing the suture in a coating solution containing a solvent and a lubricious material. Lubricious materials are commonly low molecular weight waxy aliphatic polyesters. Unfortunately the coating polymers also penetrate into the internal interstice of the suture so it is often necessary to pliabilize the sutures after coating to restore their flexibility. Although these coatings significantly reduce tissue drag, and make it easier to tie knots in these sutures, they do not completely solve the tissue abrasion and tie down issues.

Monofilament sutures provide some advantages over multifilament sutures. Monofilament sutures have a smooth uniform surface and therefore have less tissue drag. However, monofilaments tend to be stiffer and more difficult to tie secure knots than in equivalent multifilament sutures. To overcome these deficiencies in suture design several approaches have been tried.

Hunter et al. in U.S. Pat. No. 3,791,388 developed a multifilament suture that was impregnated with a binder and covered with a helical ribbon winding. Although this suture certainly improved the smoothness of multifilament sutures, the process for making this suture was slow and the binder tended to make the suture stiffer than was desirable. Schmitt et al. and Landi et al. in U.S. Pat. Nos. 3,982,543 and 4,043,344, respectively, described extruding a lubricious sheath over a multifilament core. Schmitt's approach was to use a wire coating technique like those described in U.S. Pat. Nos. 2,735,258; 2,401,291; and 2,824,485. These earlier patents describe how to make tennis strings from nylon yarns by applying multiple coats of a nylon containing solution to the nylon yarn and drying between separate application of the coating. This process provides a tough and wiry fiber well suited for tennis rackets. This process also tends to fill the interstices of the nylon yarn (see column 2 lines 20–24 of U.S. Pat. No. 2,824,485). Landi describes coating a suture by placing the suture in a split die. The die is raised to a temperature about 20° C. above the melting point of a lubricious bioabsorbable coating copolymer that has been melted and the suture is slowly passed through the molten material in the die and collecting after the coating has solidified. Unfortunately both of these process will result in the coating being distributed into the interstices of the multifilament suture which will significantly stiffen the suture.

Kurtz et al. in WO 86/00020 also describes coating multifilament sutures with film-forming materials commonly used in the construction of absorbable and non-absorbable sutures. Kurtz indicates that the coating material will penetrate and fill the interstices of the core to increase the lateral strength of the core fibers and avoid the tendencies of these core fibers to abrade, kink or fibrillate. The coating will be added in an amount sufficient to not only fill all the interstices of the multifilament core, but also to coat the surface of the yarn or thread component. In a preferred embodiment the composite so formed is further coated by melt extruding a coating material onto the composite.

Unfortunately, the helical windings and filled interstical spaces described by the prior art patent applications and patents provide a suture that is too stiff and rigid to be used in place of multifilament sutures in many surgical applications. It is an object of the present invention to provide a desirable surgical suture that combines the flexibility of multifilament sutures with the strength of monofilament sutures.

BRIEF DESCRIPTION OF THE FIGURES

FIG. 5 is a graphical presentation of a comparison of the suture roughness of a polyester suture and two coated inventive sutures.

SUMMARY OF THE INVENTION

Figure 1:
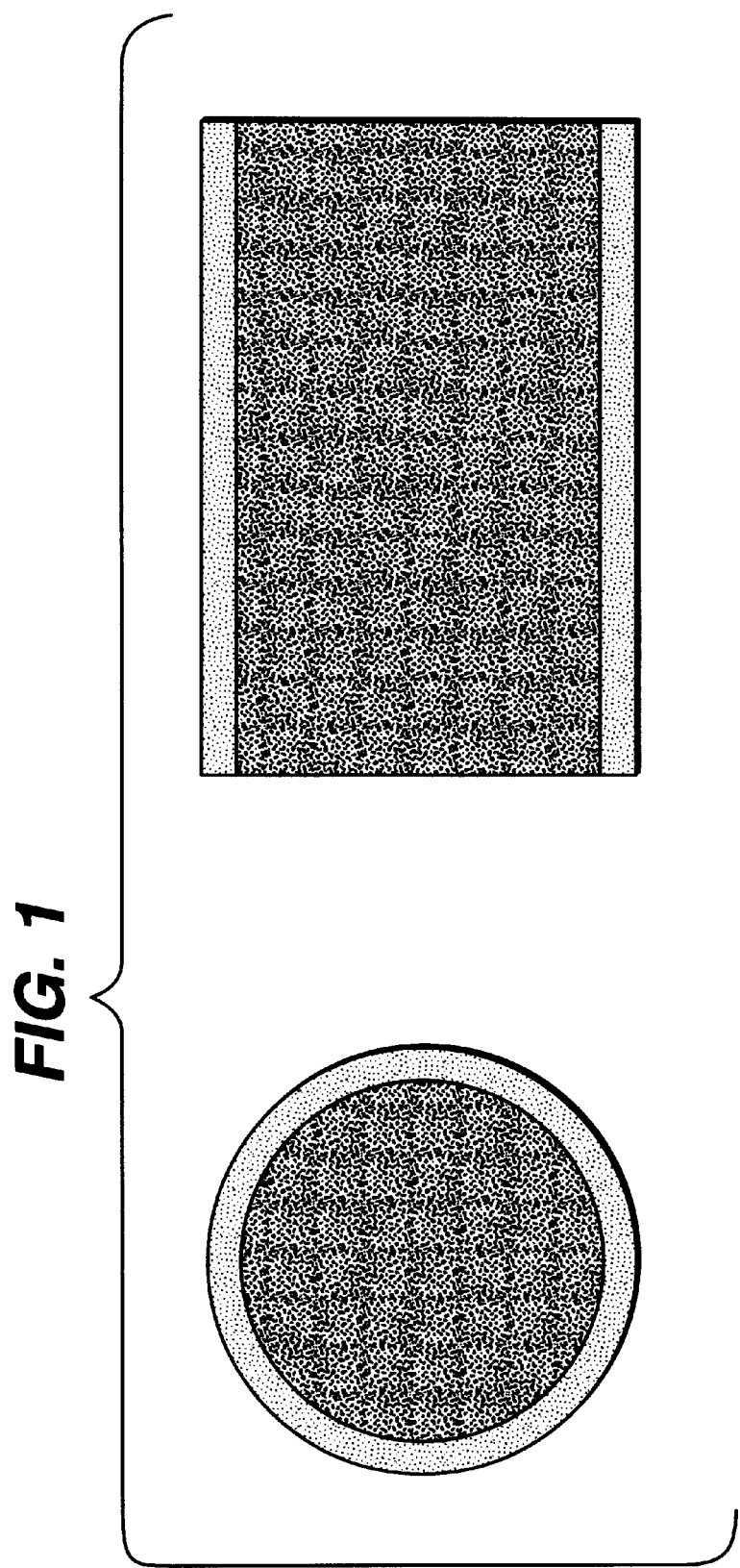
FIG. 1 is a schematic drawing of the inventive suture.
Figure 2A:
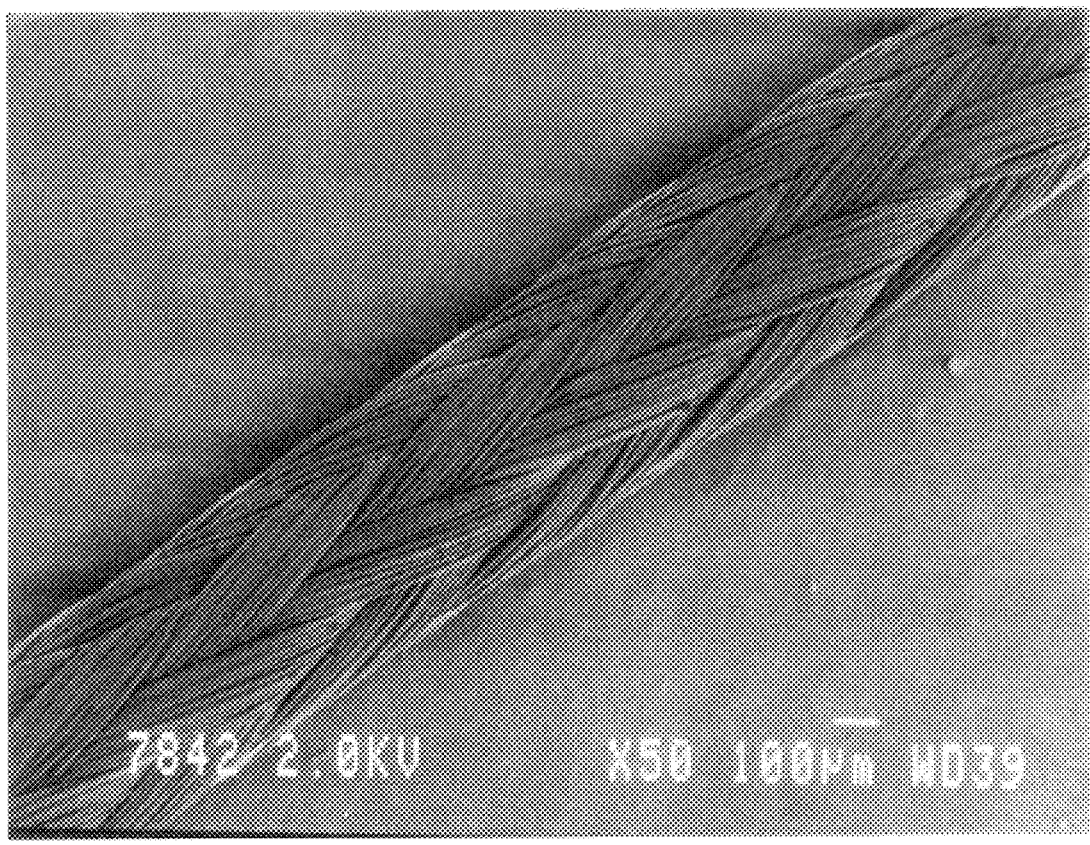
FIG. 2A is a scanning electron photomicrograph of an uncoated suture.
Figure 2B:
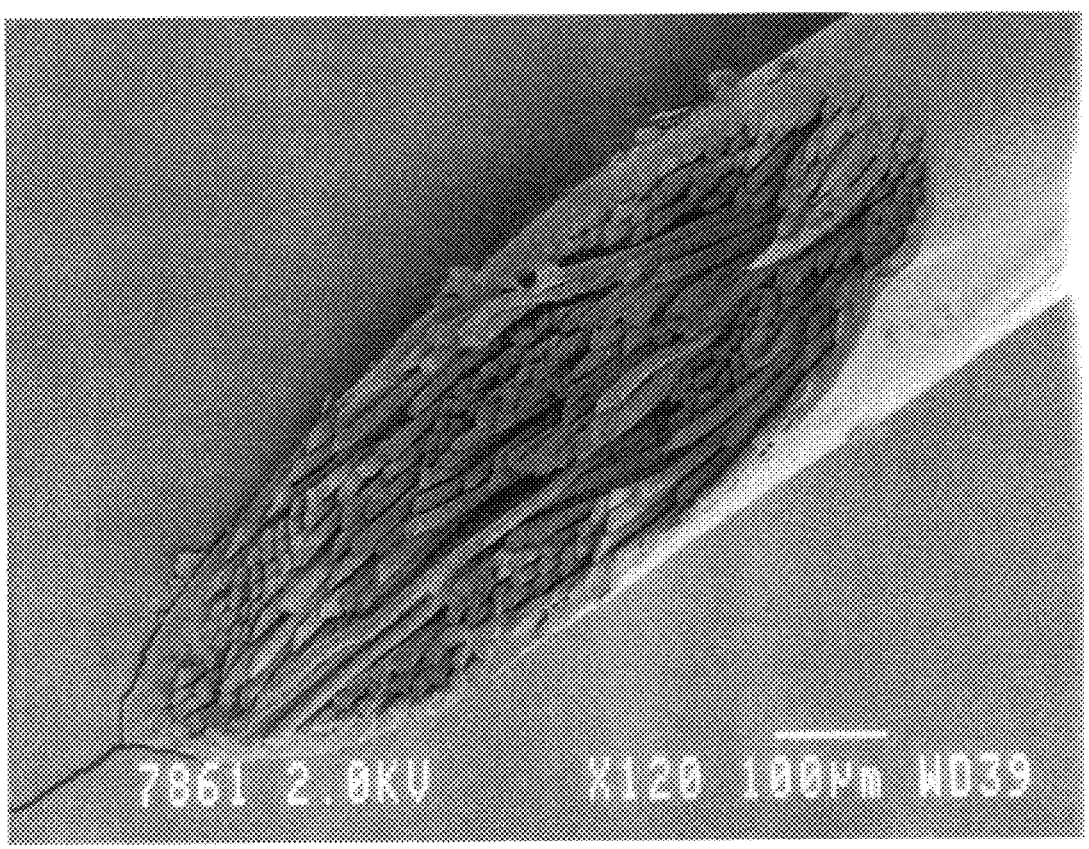
FIG. 2B is a scanning electron photomicrograph of the suture in FIG. 2A after coating which is one embodiment of the present invention.

We have discovered a surgical filament suitable for use as a suture or ligature that comprises a multifilament core having a plurality of filaments that are oriented having an external surface and internal interstices; and an outer coating that is bonded to the external surface of the core but does not penetrate into the internal interstices of the core.

We have also discovered a solvent-free process for forming surgical filaments comprising extruding a biocompatible coating on the external surface of a multifilament core having a plurality of filaments that have been previously drawn at a temperature below the melting temperature of the multifilament core wherein the biocompatible coating adheres to the external surface of the multifilament core but does not penetrate the interstices of the core.

These and other embodiments of the present invention will become readily apparent to one skilled in the art from the following Detailed Description and Examples.

DETAILED DESCRIPTION

The core of the surgical ligature may be composed of any suitable biocompatible multifilament assembly that is oriented. The multifilament core can be a bundle of individual filaments, a yarn or tow (that may be entangled, twisted or plied) or filaments or yarns that have been braided, knitted or woven. Currently it is preferred to use a braided or knitted ligature made from a plurality of yarns. Suitable braided constructions for suture are described in U.S. Pat. Nos. 5,019,093; 5,059,213 and 4,959,069 (the disclosures of which are hereby incorporated by reference herein). At least one of the filaments in the multifilament core should be oriented so that a significant number of the molecules within the fiber are positioned substantially parallel to the length of the fiber to impart strength parallel to the fibers length. Preferably a significant number of the core filaments will be oriented to provide strength to the inventive suture and most preferably all of the core filaments will be oriented. Synthetic fibers the filaments are generally drawn at least 2 times their original length to orientation the molecules in the fibers and preferably in the range of about 2 to about 20 times their original length. Some processing techniques allow even higher draw ratios. Suitable methods for forming and orienting the biocompatible fibers are well known in the art. Suitable multifilament biocompatible ligature materials are also well known in the art. Examples of nonabsorbable ligature materials include, but are not limited to, silk, polyesters (such as polybutylene terephthalate, polyethylene terephthalate, polybutester (such as Hytrel™ polybutester manufactured by DuPont, DE, USA and blends thereof), polyvinylidene fluoride and copolymers thereof (as is described in U.S. Pat. Nos. 4,564,013 and 5,219,659 which are incorporated herein), polyolefins (such as polyethylene, polypropylene and copolymers thereof as described in U.S. Pat. Nos. 4,520,822 and 4,557,264 which are incorporated herein), polyamides (such as nylons e.g. nylon 6, nylon 66, nylon 610, nylon 12, etc. and aromatic polyamides as described in WO 86/00020 which is incorporated herein). Silk is generally described as a nonabsorbable suture material, however, current evidence indicates that it is degraded by the body. Examples of absorbable ligature materials include but are not limited to homopolymers, copolymers (including polymers containing two or more monomers having random and non-random structures) and blends of aliphatic polyesters, polyoxaesters, polyoxaamides, polyoxaesters containing amido groups, polyanhydrides, polyorthoesters, and combinations thereof. Suitable aliphatic polyesters may be make from monomers that generally have the formula:

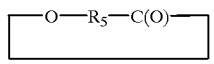

VIII

These monomers (or equivalent acids if any) may be polymerized to provide polymers of the following general structures:

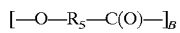

IX

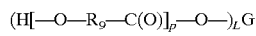

X wherein $R_5$ and $R_9$ are independently selected from the group consisting of $-CH_2-CH_2-O-CH_2-$, $-CR_8H-CH_2-$, $-(CH_2)_3-O-$, $-C(R_6)(R_7)-$, $-C(R_6)(R_7)-C(O)-O-C(R_6)(R_7)-$, $-(CH_2)_K-C(O)-CH_2-$, $-(CH_2)_5-$, $-(CH_2)_F-O-C(O)-$; and $R_6$ and $R_7$ are independently selected from the group consisting of hydrogen and an alkyl containing from 1 to 8 carbon atoms; $R_8$ is selected from the group consisting of hydrogen and methyl; F and K are integers in the range of from 2 to 6; B is an integer in the range of from 1 to n such that the number average molecular weight of formula IX is less than about 500,000, preferably less than about 80,000; P is an integer in the range of from 1 to m such that the number average molecular weight of formula X is less than about 1,000,000, preferably less than about 200,000, preferably less than about 40,000 and most preferably less than 20,000; G represents the residue minus from 1 to L hydrogen atoms from the hydroxyl groups of an alcohol previously containing from 1 to about 200 hydroxyl groups; and L is an integer from about 1 to about 2. Preferably G will be the residue of a dihydroxy alcohol minus both hydroxyl groups. Suitable monomers include lactic acid, lactide (d, l and meso lactide and blends thereof), glycolic acid, glycolide, ϵ-caprolactone, p-dioxanone, 6,6-dimethyl-1,4-dioxepan-2-one, trimethylene carbonate, 1,4-dioxepan-2-one, 1,5-dioxepan-2-one and combinations thereof.

The biocompatible coating may be utilize the same biocompatible synthetic polymers described above for use in making the core filaments provided that the temperature that the core filaments will be exposed to during coating does not melt the core filaments or substantially reduce the molecular orientation of the polymer chains of the core filaments. For the purpose of this invention the coating forms a surface that is independent of the underlying shape of the filament core but bonded to the external surface of the core. The coating layer is preferably melt coated onto the external surface of the core filaments to provide a cross section of the desired shape such as a circle, a triangle with rounded corners, polygonal or other desired shape. A smoother surface is provided thereby reducing the tissue drag associated with multifilament suture. Additionally, because only the external surface of the core is bonded to the coating layer the internal filaments in the core are free to move and provide flexibility to the ligature. The coating, however, should be bonded to the core's external surface so that it will not peel, strip or separate after tying at least 4 throws (two complete surgeon's square knots). Example 8 describes how these knots are tied.

The coating thickness should be sufficient to substantially reduce or eliminate the hills and valleys normally associated with the surfaces of multifilament constructions. To fill in the space between the filaments in the core and provide the desired smooth external surface, the coating layer thickness generally should average at least ¼ of the diameter of the filaments used in the core and preferably will average at least ½ of the diameter of the filaments used in the core. The coating layer thickness for ligatures constructed from yarns (i.e. with a diameter of about 13 microns) will generally average from about 5 microns to about 125 microns and preferably will average in the range of from about 5 to about 25 microns.

The biocompatible synthetic polymers used in the coating layer may be homopolymers, copolymers or blends of the previously described biocompatible polymers used in making the core filaments. The coating layer must be formed from a non-friable biocompatible synthetic polymer. Generally, but in no way limiting the scope of this invention, we believe that polymers with a molecular weight of greater than 10,000 will be preferred for use as coating polymers.

If the coating layer is bioabsorbable it may also contain various medicaments (such as antimicrobial agents i.e. antibiotics or silver compounds) therapeutic (such as antiinflammatory agents) and other biologically active materials (such as growth factors). The outer surface of the coated ligature may also be coated with an additional lubricant to further enhance its knot slide.

Figure 3:
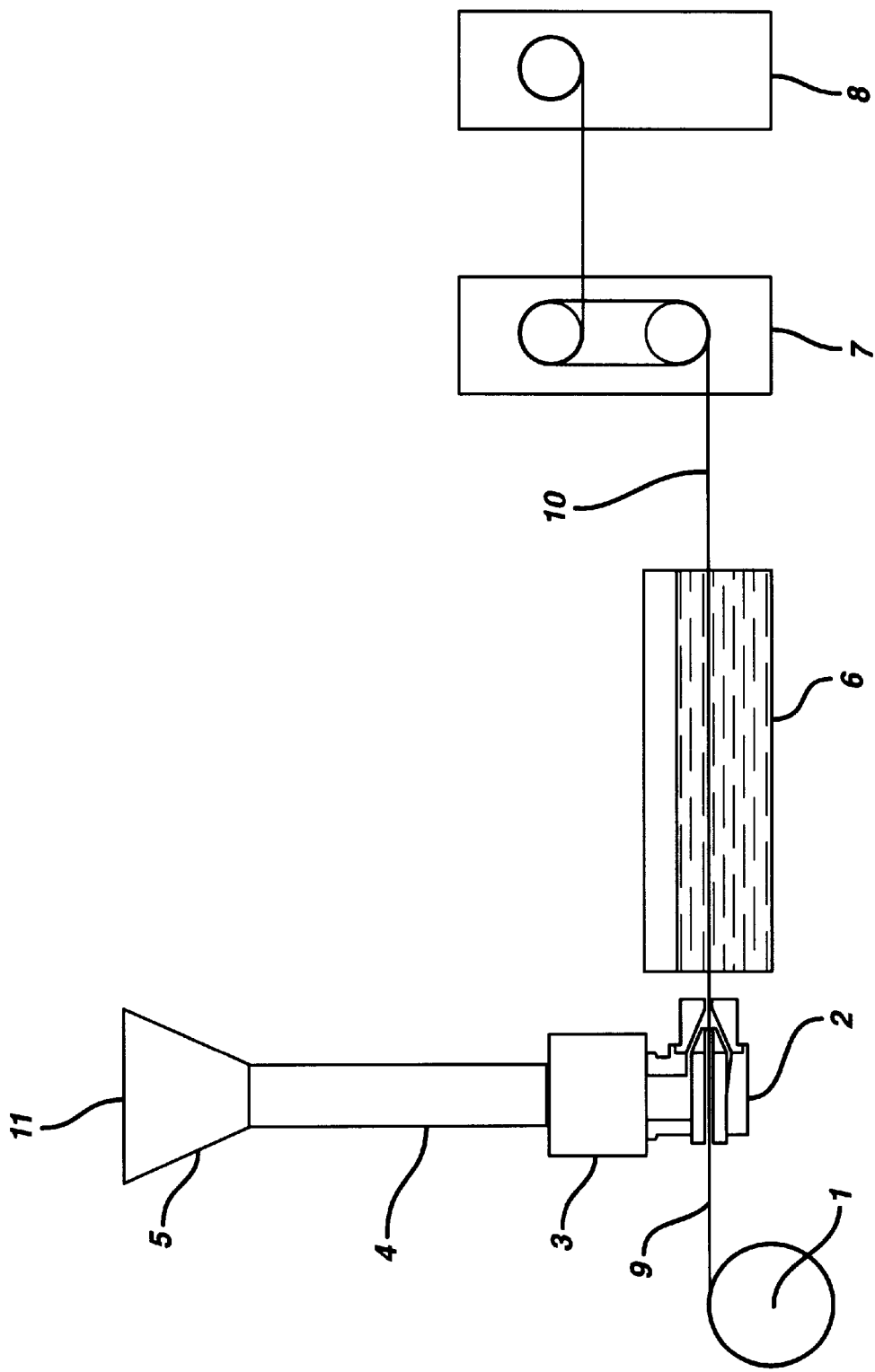
FIG. 3 is a schematic drawing that illustrates one process for manufacturing the inventive sutures.
Figure 4:
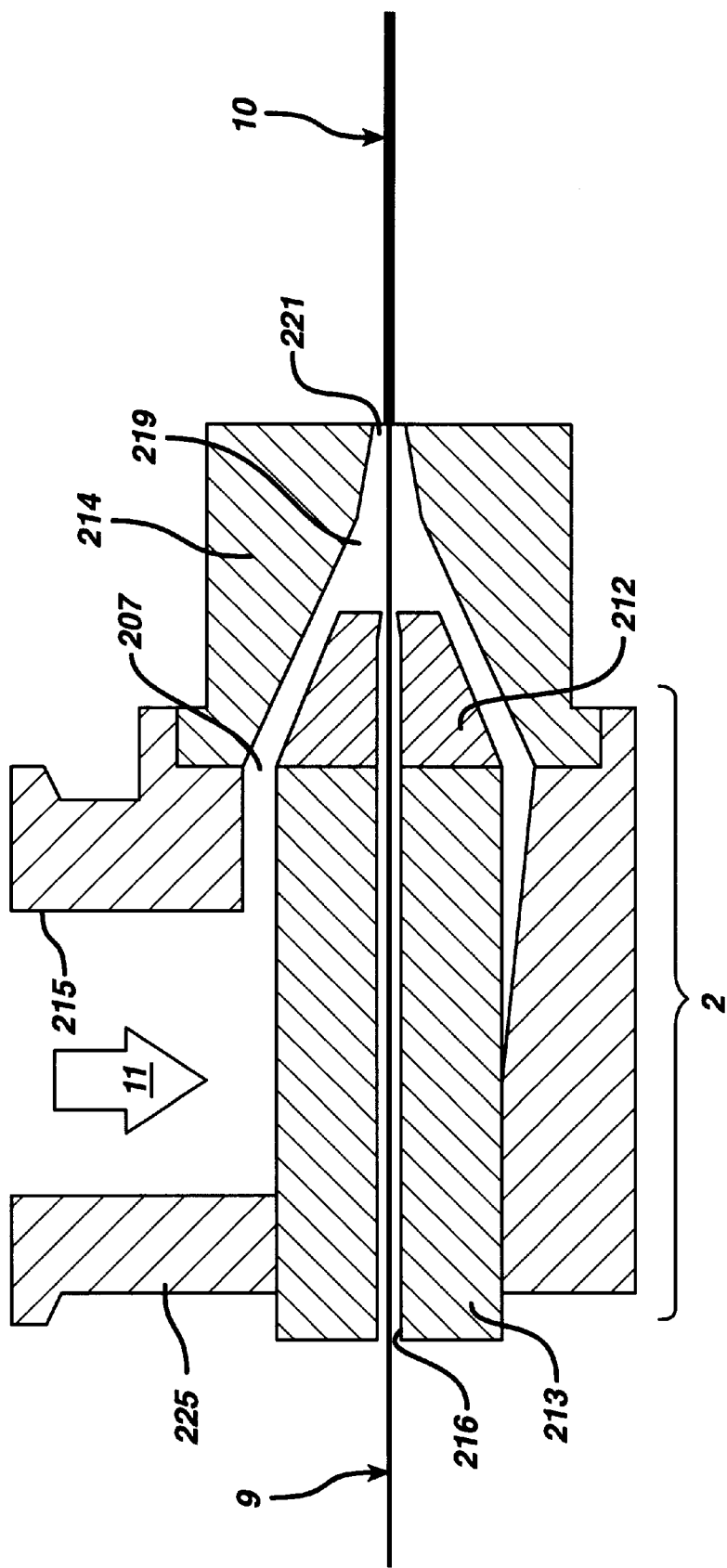
FIG. 4 is an enlarged schematic drawing of melt coating die assembly 2.

In one embodiment of the present invention as illustrated in FIGS. 3 and 4. In FIG. 3 the uncoated filaments 9 are taken from a spool 1 and passed through a melt coating die assembly 2 to be coated with a coating material 11. The spool may have a frictional brake or other tensioning device to assure a uniform feed rate of the filaments into the melt coating die assembly 2. Suitable melt coating dies are commercially available from Canterberry Engineering, USA. The coating material 11 is feed into hopper 5. The coating material 11 will pass from hopper 5 into extruder barrel 4 and be melted. The melted coating material 11 will them be pumped at a constant pressure or rate through a melt metering device 3 to coating die assembly 2. As is illustrated in FIG. 4 the melted coating material 11 is pumped into inlet 215 of the coating die assembly body 225 and passes through passage way 207 to chamber 219 where the melted coating material 11 contact the uncoated filaments 9. The uncoated filaments enter the coating assembly 2 through passage 216 in the core tube 213. Attached to the end of the core tube is a tapered guider tip 212, which terminates in chamber 219. Chamber 219 is bounded by guider tip 212 and die 214 that are adjustably maintained in position by the coating die assembly 225. The uncoated filaments 9 contact the melted coating material in chamber 219, become coated with the melt coating material 11 and pass through the chamber to outlet 221. The coated ligature 10 is then cooled to solidify the melted coating material preferably in a liquid bath 6. Once the coating material has solidified on the coated filaments the coated filaments are collected preferably by passing the coated ligature over godets rolls 7 then on to a take-up stand 8.

In another embodiment of the present invention which is not specifically illustrated, the guider tip 212 could extend to outlet 221 where the uncoated core filaments would first contact the melted coating material 11.

Additionally, the surgical filament may be woven or knitted into various surgical textiles such as barriers, scaffolds, meshes, and the like, and having coating and film added thereto. The surgical textiles may thereafter be further processed. The following non-limiting examples are provided to further illustrate the practice of the present invention.

EXAMPLE 1

An absorbable melt coated ligature was made from a 75/25 poly(glycolide—co—caprolactone) segmented copolymer coated onto a 90/10 poly(glycolide-co-lactide) random copolymer braided multifilament substrate. The 75/25 poly(glycolide—co—caprolactone) segmented copolymer is used to make Monocryl™ Suture, sold by ETHICON, Inc. of Somerville, N.J., and described in U.S. Pat. No. 5,133,739, issued Jul. 28, 1992, Bezwada et al. assigned to Ethicon.

The 90/10 poly(glycolide—co—lactide) random copolymer braided multifilament substrate was that from which Vicryl™ Suture, sold by ETHICON, Inc. of Somerville, N.J., is made. This size 3/0 material would generally need to be solution coated with a lubricious coating, cut to length, needles attached, packaged, sterilized and sealed, to complete the existing manufacturing process.

In one embodiment of the present invention, the braided multifilament substrate was instead subjected to a melt coating process that bonded an outer coating to the external surface of the multifilament substrate (or core), but did not penetrate into the internal interstices of the core.

An extruder with a 1" diameter screw (Killion Extruder) was used with a pressure guider and die (Canterberry Engineering, P/N CEC 10177 and CEC 10124). The coating material (75/25 poly(glycolide—co—caprolactone) copolymer), in pellet form, was fed into the extruder hopper. The hopper was provided with a constant flow of nitrogen. The substrate was then fed through the pressure guider and die by attaching the substrate to a metallic guide wire and pushing the wire through the assembled guider. Another method used to feed the substrate through the guider and die involved feeding the substrate through the guider and die prior to assembly in the extruder. Once the substrate was fed, the guider and die were assembled into the extruder. The substrate was then fed through the rest of the coating line including the water bath, laser micrometer, godet rolls and take up unit. As is illustrated in FIG. 3. The coating material passed through the hopper into the extruder barrel and was melted. The melted material was then pumped at a constant rate through a melt-metering device. The melted coating material was then pumped around the guider tip and through the die where it encompassed the uncoated substrate and creates a coated structure. The take-up speeds and extrusion parameters were altered until a smooth and uniform coating was established. The conditions were monitored and documented in Table 1.

TABLE 1

Processing Conditions for a (75/25 PGA/PCL) polymer outer coating over a braided, size 3/0, 90/10 poly (glycolide-co-lactide) random copolymer multifilament core:

| Process Conditions | |
| --- | --- |
| Melt Temperature (° F.) | 350 |
| Die Temperature (° F.) | 340 |
| Pump Temperature (° F.) | 360 |
| Block Temperature (° F.) | 380 |
| Barrel Temperature - Zone 3 (° F.) | 410 |
| Barrel Temperature - Zone 2 (° F.) | 400 |
| Barrel Temperature - Zone 1 (° F.) | 370 |
| Barrel Pressure (psi) | 2500 |
| Pump Pressure (psi) | 2500 |
| Die Pressure (psi) | 850 |
| Take-up Speed (fpm) | 23–39 |
| Die Orifice (mils) | 14 |

EXAMPLE 2

A non-absorbable polyester ligature was made using a copolyester-ether elastomer coating material over a 20 polyethylene terephthalate braided substrate. The copolyester-ether elastomer is commercially available from Hoechst Celanese and was sold under the tradename Riteflex™ 655. The Riteflex™ 655 material is a copolyester thermoplastic elastomer with a hard and soft segment as shown below:

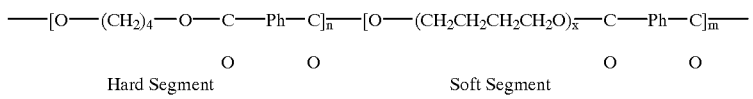

Hard Segment          Soft Segment

The polyethylene terephthalate braided structure is based on commercially available suture material from Ethicon Inc. (Somerville, N.J., USA), size 3/0 Mersilene™ Polyethylene Terephthalate Suture. The procedure followed is identical to that described in Example one with the exception of the processing conditions which are listed in Table 2. The processing conditions were altered, especially the extrusion temperatures and take up speed, to provide a smooth uniform outer surface.

TABLE 2

Processing conditions for a Riteflex ™ 655 (copolyester - ether elastomer - Hoechst Celanese) polymer coating over a 3/0 Mersilene ™ PET) Suture:

| Process Conditions | |
|---|---|
| Melt Temperature (° F.) | 420 |
| Die Temperature (° F.) | 410 |
| Pump Temperature (° F.) | 440 |
| Block Temperature (° F.) | 440 |
| Barrel Temperature - Zone 3 (° F.) | 420 |
| Barrel Temperature - Zone 2 (° F.) | 420 |
| Barrel Temperature - Zone 1 (° F.) | 400 |
| Barrel Pressure (psi) | 2500 |
| Pump Pressure (psi) | 400 |
| Die Pressure (psi) | 400 |
| Take-up Speed (fpm) | 23 |
| Die Orifice (mils) | 14 |

EXAMPLE 3

A non-absorbable ligature was made of an Ethylene-propylene copolymer coating material over a PET braided substrate. The Ethylene-propylene copolymer is commercially available from Exxon under the name Exact 3035 and can be represented as:

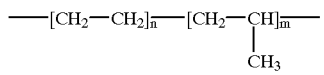

The procedure followed is identical to that described in Example one with the exception of the processing conditions which are listed in Table 3. The processing conditions were altered, especially the extrusion temperatures and take up speed, to provide a smooth uniform outer surface.

TABLE 3

Processing conditions for EXACT 3035 (Ethylene-propylene copolymer - Exxon) coating over a 3/0 Mersilene ™ (PET) Suture:

| Process Conditions | |
|---|---|
| Melt Temperature (° F.) | 400 |
| Die Temperature (° F.) | 400 |
| Pump Temperature (° F.) | 400 |
| Block Temperature (° F.) | 400 |
| Barrel Temperature - Zone 3 (° F.) | 400 |
| Barrel Temperature - Zone 2 (° F.) | 390 |
| Barrel Temperature - Zone 1 (° F.) | 380 |
| Barrel Pressure (psi) | 2500 |
| Pump Pressure (psi) | 3000 |
| Die Pressure (psi) | 3000 |
| Take-up Speed (fpm) | 23–110 |
| Die Orifice (mils) | 14 |

EXAMPLE 4

An absorbable ligature was made of a poly(p-dioxanone) coating material over a 90/10 PGA/PLA substrate. The poly(p-dioxanone) polymer can be represented as:

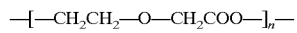

The procedure followed is identical to that described in Example 1 with the exception of the processing conditions which are listed in Table 4. The processing conditions were altered, especially the extrusion temperatures and take up speed, to provide a smooth uniform outer surface.

TABLE 4

Processing Conditions for a Poly (p-dioxanone) polymer coated over a Size 1 (90/10 PGA/PLA) Suture

| Process Conditions | |
|---|---|
| Melt Temperature (° F.) | 260 |
| Die Temperature (° F.) | 260 |
| Pump Temperature (° F.) | 260 |
| Block Temperature (° F.) | 260 |
| Barrel Temperature - Zone 3 (° F.) | 260 |
| Barrel Temperature - Zone 2 (° F.) | 255 |
| Barrel Temperature - Zone 1 (° F.) | 250 |
| Barrel Pressure (psi) | 1500 |
| Pump Pressure (psi) | 3800 |
| Die Pressure (psi) | 3200 |
| Take-up Speed (fpm) | 40 |
| Die Orifice (mils) | 26 |

EXAMPLE 5

A non-absorbable ligature was made by coating polypropylene polymer over a polyethylene terephthalate braided substrate. The polypropylene material can be represented as:

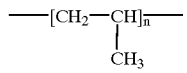

The polyethylene terephthalate braided structure is based on commercially available suture material from Ethicon Inc. (Somerville, N.J., USA), size 3/0 suture sold identified as Mersilene™ Polyethylene Terephthalate Suture. The procedure followed is identical to that described in Example one with the exception of the processing conditions which are listed in Table 5. The processing conditions were altered, especially the extrusion temperatures and take up speed, to provide a smooth uniform outer surface.

TABLE 5

Processing Conditions for a Polypropylene (Homopolymer - Aristech) polymer coated over Size 1 Mersilene ™ (PET) Suture:

| Process Conditions | |
|---|---|
| Melt Temperature (° F.) | 380 |
| Die Temperature (° F.) | 390 |
| Pump Temperature (° F.) | 395 |
| Block Temperature (° F.) | 390 |
| Barrel Temperature - Zone 3 (° F.) | 395 |
| Barrel Temperature - Zone 2 (° F.) | 390 |
| Barrel Temperature - Zone 1 (° F.) | 360 |
| Barrel Pressure (psi) | |
| Pump Pressure (psi) | 500 |
| Die Pressure (psi) | 250 |

TABLE 5-continued

Processing Conditions for a Polypropylene
(Homopolymer - Aristech) polymer coated over
Size 1 Mersilene ™ (PET) Suture:

Process Conditions

| | |
|---|---|
| Take-up Speed (fpm) | 100 |
| Die Orifice (mils) | 26 |

EXAMPLE 6

A non-absorbable ligature was made of a high density polyethylene coating material over a braided PET substrate. The coating material was a High Density Polyethylene (HDPE) and can be represented as:

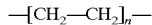

The polyethylene terephthalate braided structure is based on commercially available suture material from Ethicon Inc. (Somerville, N.J., USA), size 2/0 Mersilene™ Polyethylene Terephthalate Suture. The procedure followed is identical to that described in Example one with the exception of the processing conditions which are listed in Table 6. The processing conditions were altered, especially the extrusion temperatures and take up speed, to provide a smooth uniform outer surface.

TABLE 6

Processing Conditions for a High Density Polyethylene
(HDPE - Union Carbide) polymer coating over Size 2–0
Mersilene ™ Polyethylene Terephthalate Suture:

Process Conditions

| | |
|---|---|
| Melt Temperature (° F.) | 510 |
| Die Temperature (° F.) | 530 |
| Pump Temperature (° F.) | 515 |
| Block Temperature (° F.) | 515 |
| Barrel Temperature - Zone 3 (° F.) | 500 |
| Barrel Temperature - Zone 2 (° F.) | 475 |
| Barrel Temperature - Zone 1 (° F.) | 330 |
| Barrel Pressure (psi) | |
| Pump Pressure (psi) | 1850 |
| Die Pressure (psi) | 1500 |
| Take-up Speed (fpm) | 800 |
| Die Orifice (mils) | 26 |

EXAMPLE 7

A absorbable ligature was made of 85/15 poly (paradioxanone—co—lactide) copolymer coating material over a braided 90/10 poly(glycolide—co—lactide) random copolymer substrate. An extruder with a ⅝" diameter screw (Randcastle Extruder) with a sleeving die (Canterbury Engineering, CEC sleeving guider—0.014×0.054 and sleeving die 0.059) was used. The coating material was fed into the hopper. The coating material passed from the hopper into the extruder barrel and was melted. The substrate was then fed through the pressure guider and die by attaching the suture to a metallic guide wire and pushing the wire through the assembled guider. Another method used to feed the substrate through the guider and die involved feeding the substrate through the guider and die prior to assembly in the extruder. Once the substrate was fed, the guider and die were assembled into the extruder. The substrate was then fed through the rest of the coating line including the water bath, laser micrometer, godet rolls and take up unit. The melted coating material was then pumped at a constant pressure through a melt metering device to the coating die assembly. The melted coating was then pumped around the guider tip and through the die where it then encompassed the uncoated substrate and created a coated structure. The coated structure was then cooled to solidify the melted coating material in a water bath. The take-up speed and extrusion parameters were altered until a smooth and uniform coating was established. The conditions were monitored and documented in Table 7.

TABLE 7

Processing Conditions for a Absorbable coating 85%/15%
para-dioxanone-co-lactide copolymer over Size 2–0
suture made from a 90/10 glycolide-co-lactide copolymer:

Process Conditions

| | |
|---|---|
| Melt Temperature (° F.) | 290 |
| Die Temperature (° F.) | 280 |
| Barrel Temperature (° F.) Zone 3 | 280 |
| Barrel Temperature (° F.) Zone 2 | 270 |
| Barrel Temperature (° F.) Zone 1 | 220 |
| Melt Pressure (psi) | 1000 |
| Screw Speed (rpm) | 0.3 |
| Screw draw (amps) | 0.5 |
| Take-up Speed (fpm) | 9.5 |
| Die Diameter (in) | 0.070 |
| Guider dimensions (in.) | 0.040 × 0.060 |

EXAMPLE 8

The suture knot strength was determined by the following procedures:

A single suture is tied in a surgeon's square knot around an 8 mm in diameter mandrel. The square knot is tied in a consistent manner (left over right, right over left) and pulled taut after each throw.

EXAMPLE 9

Suture roughness tests, as reported in FIG. 5, were determined using the testing procedures described in U.S. Pat. No. 4,027,676, except that the roughness number presented in the FIG. was the average of the roughness (see FIG. 3 of U.S. Pat. No. 4,027,676) from the zero point.

We claim:

1. A surgical filament suitable for use as a suture or ligature that comprises a multifilament core having a plurality of filaments that are oriented having an external surface and internal interstices; and an outer coating that bonded to the external surface of the core but does not penetrate into the internal interstices of the core.

2. The surgical filament of claim 1 wherein the multifilament core is braided.

3. The surgical filament of claim 1 wherein the multifilament core is yarn selected from the group consisting of entangled, twisted and plied yarns.

4. The surgical filament of claim 1 wherein the multifilament core is knitted.

5. The surgical filament of claim 1 wherein the multifilament core contains nonabsorbable filaments.

6. The surgical filament of claim 5 wherein the multifilament core is nonabsorbable filaments made from nonabsorbable materials selected from the group consisting of silk, polyesters, polyvinylidene fluoride and polyvinylidene copolymers, polyolefins, polyamides and combinations thereof.

7. The surgical filament of claim 1 wherein the multifilament core contains absorbable filaments.

8. The surgical filament of claim 5 wherein the multifilament core is absorbable filaments made from absorbable materials selected from the group consisting of homopolymers, copolymers and blends of aliphatic polyesters, polyoxaesters, polyoxaamides, polyoxaesters containing amido groups, polyanhydrides, polyorthoesters, and combinations thereof.

9. The surgical filament of claim 5 wherein the multifilament core is composed of absorbable filaments made from an aliphatic polyester.

10. The surgical filament of claim 5 wherein the multifilament core is absorbable filaments made from an aliphatic polyester selected from the group consisting of lactic acid, lactide (d, l and meso lactide and blends thereof), glycolic acid, glycolide, ε-caprolactone, p-dioxanone, 6,6-dimethyl-1,4-dioxepan-2-one, trimethylene carbonate, 1,4-dioxepan-2and combination thereof.

11. The surgical filament of claim 1 wherein the outer coating is nonabsorbable.

12. The surgical filament of claim 11 wherein the nonabsorbable outer coating is made from a material selected from the group consisting of silk, polyesters, polyvinylidene fluoride and polyvinylidene copolymers, polyolefins, polyamides and combinations thereof.

13. The surgical filament of claim 1 wherein the outer coating is absorbable.

14. The surgical filament of claim 13 wherein the outer coating is made from absorbable materials selected from the group consisting of homopolymers, copolymers and blends of aliphatic polyesters, polyoxaesters, polyoxaamides, polyoxaesters containing amido groups, polyanhydrides, polyorthoesters, and combinations thereof.

15. The surgical filament of claim 14 wherein the outer coating is made from an absorbable aliphatic polyester.

16. The surgical filament of claim 15 wherein the outer coating is made with an aliphatic polyester selected from the group consisting of lactic acid, lactide (d, l and mesa lactide and blends thereof), glycolic acid, glycolide, ε-caprolactone, p-dioxanone, 6,6-dimethyl-1,4-dioxepan-2-one, trimethylene carbonate, 1,4-dioxepan-2-one, 1,5- dioxepan-2-one and combinations thereof.

17. A process for forming a surgical filament suitable for use as a suture or ligature comprising: meltcoating the external surface of an oriented biocompatible multifilament core with a melted biocompatible polymer wherein the melted biocompatible polymer is cooled to form an outer coating that bonds to the external surface of the multifilament core but does not penetrate into the internal interstices of the multifilament core.

* * * * *